United States Patent [19]

Ryang

[11] Patent Number: 4,533,737
[45] Date of Patent: * Aug. 6, 1985

[54] SILICON FUNCTIONALIZED NORBORNANE CARBOXYIMIDE AND METHODS FOR MAKING

[75] Inventor: Hong-Son Ryang, Camarillo, Calif.

[73] Assignee: General Electric Company, Schenectady, N.Y.

[*] Notice: The portion of the term of this patent subsequent to Sep. 18, 2001 has been disclaimed.

[21] Appl. No.: 596,187

[22] Filed: Apr. 2, 1984

[51] Int. Cl.$^3$ ............................................... C07F 7/10
[52] U.S. Cl. .................................................... 548/110
[58] Field of Search ........................................ 548/110

[56] References Cited

U.S. PATENT DOCUMENTS

| | | | |
|---|---|---|---|
| 4,238,591 | 12/1980 | Eassat et al. | 528/27 |
| 4,360,686 | 11/1982 | Wang et al. | 548/110 |
| 4,361,690 | 11/1982 | Locatelli | 528/27 |
| 4,472,565 | 9/1984 | Ryang | 525/431 |

Primary Examiner—Joseph L. Schofer
Assistant Examiner—Peter F. Kulkosky
Attorney, Agent, or Firm—William A. Teoli; James C. Davis, Jr.; James Magee, Jr.

[57] ABSTRACT

Silicon functionalized carboxyimides are provided which can be made by the hydrosilylation of norbornene terminated polyimides with silicon hydrides having hydrolyzable radicals attached thereto. The silicon functionalized carboxyimides can be used to make silanol terminated silicon-polyimide block polymers useful in making room temperature vulcanizable compositions.

8 Claims, No Drawings

SILICON FUNCTIONALIZED NORBORNANE CARBOXYIMIDE AND METHODS FOR MAKING

CROSS REFERENCE TO RELATED APPLICATIONS

Reference is made to my copending applications Ser. No. 395,932, filed July 7, 1982, now U.S. Pat. No. 4,381,396, for Silylnorbornane Anhydrides and Method for Making and Ser. No. 953,933, filed July 7, 1982, now U.S. Pat. No. 4,404,350, for Silicon-imide Copolymers and Method for Making, both applications being assigned to the same assignee as the present invention.

BACKGROUND OF THE INVENTION

The present invention relates to norbornanecarboxyimide having silicon functional groups, and methods for making and modifying such materials. In addition, the present invention relates to use of such silicon containing norbornanecarboxyimide to make silanol terminated polydiorganosiloxanepolyimide block polymers and room temperature vulcanizable compositions (RTV's) resulting therefrom.

Prior to the present invention, room temperature vulcanizable silanol terminated polydiorganosiloxanes, for example, silanol terminated polydimethylsiloxanes were available in either one-package or two-package systems based on the nature of the moisture sensitive cross-linking agents utilized in the composition. A typical one-package system is based on the use of methyltriacetoxysilane and a silanol terminated polydimethylsiloxane as shown by Ceyzeriat, U.S. Pat. No. 3,133,891. A two-package system as shown by Nitzsche et al., U.S. Pat. No. 3,065,194 requires the blending of silanol terminated polydimethylsiloxane with a curing catalyst, such as ethyl orthosilicate in combination with dibutyltindilaurate. The two-package system requires mixing of the curing catalyst with the silanol terminated polydimethylsiloxane prior to use.

The above described one-package and two-package room temperature vulcanizable compositions generally require the use of reinforcing filler, for example, a silica filler in amounts of from 5-300 parts, per 100 parts of silicone polymer, if improved tensile strength in the resulting cured silicone is desired. Another procedure available to improve the toughness of cured silicone polymers in the introduction of silarylenesiloxy units into the polymer chain to produce a copolymer consisting essentially of diorganosiloxy units chemically combined with silarylenesiloxy units. Although these procedures substantially enhance the modulus (psi) of the silicone polymer, these procedures are uneconomic or do not achieve the degree of physical properties desired in the end product.

As taught in my copending application RD-15535, silicon hydride terminated polyimide having the formula,

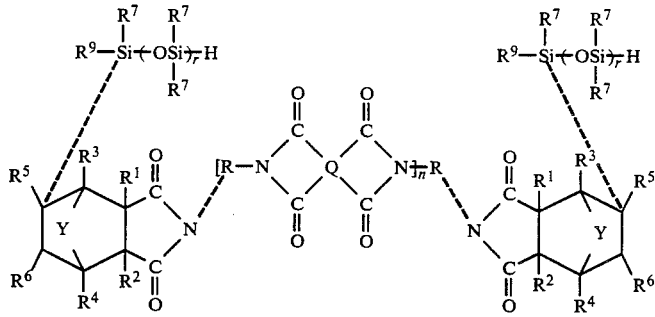

can be used to prepare silanol terminated polydiorganosiloxane polyimide copolymers useful for making high strength RTV compositions, where R is a divalent radical selected from the class consisting of (a) aromatic hydrocarbon radicals having from 6-20 carbon atoms and halogenated aromatic hydrocarbon radicals having from 6-20 carbon atoms, (b) alkylene radicals having from 2-20 carbon atoms and cycloalkylene radicals having from 2-20 carbon atoms, (c) $C_{(2-8)}$ alkylene terminated polydiorganosiloxane, and (d) radicals included by the general formula,

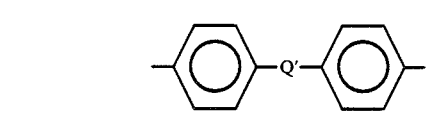

Q' is a member selected from the class consisting of

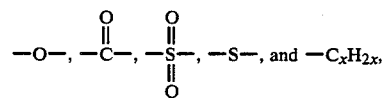

x is a whole number from 1 to 5 inclusive, Q is a tetravalent radical selected from

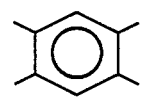

and

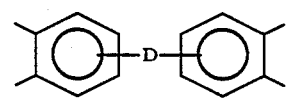

where D is a member selected from

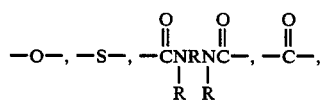

-continued $$-\overset{O}{\underset{\|}{C}}-OR^8O\overset{O}{\underset{\|}{C}}- \quad \text{and} \quad -OR^8O-$$

and $R^8$ is a divalent radical selected from

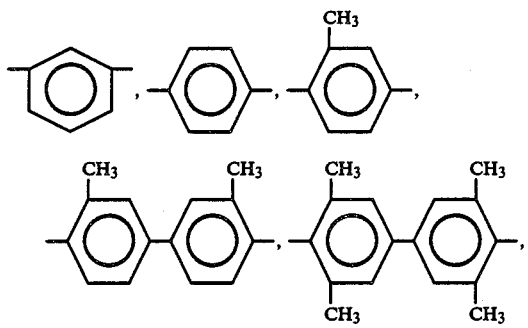

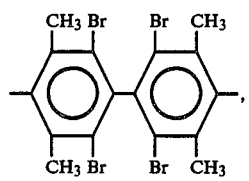

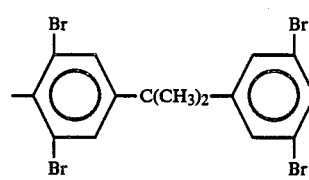

and divalent organic radicals of the general formula,

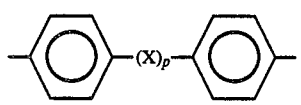

X is a member selected from the class consisting of divalent radicals of the formula,

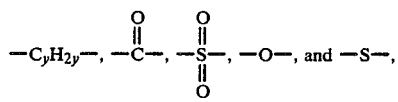

y is an integer from 1 to 5, $R^1$-$R^6$ are selected from hydrogen and $C_{(1-8)}$ alkyl radicals, $R^7$ is the same or different $C_{(C1-13)}$ monovalent hydrocarbon radical and substituted $C_{(1-13)}$ monovalent hydrocarbon radical, -$R^9$ is selected from H or $R^7$ Y is a divalent radical selected from —O— and —C($R^1$)$_2$—, n is an integer equal to 0–200 inclusive, and r and p are whole numbers equal to 0 or 1.

The present invention is based on my discovery that high strength silicon-polyimide copolymer products also can be made by effecting the cure of room temperature or low temperature condensation vulcanizable silanol terminated polydiorganosiloxane-polyimide copolymers resulting from the reaction of silanol terminated polydiorganosiloxane of the formula

 (1)

with silicon functionalized norbornane carboxyimide referred to hereinafter as "silicon-norbornanebisimide" of the formula

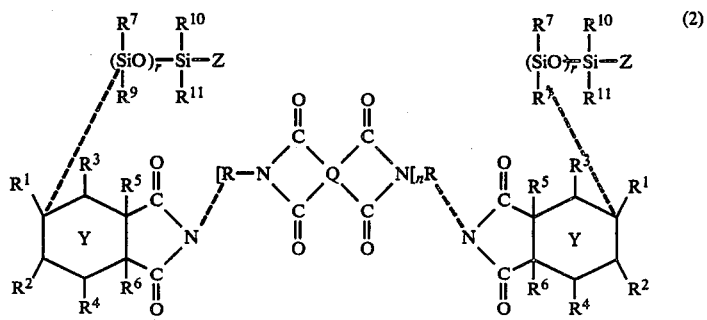 (2)

where R-$R^7$ are as previously defined, Z is selected from $C_{(1-8)}$ alkoxy, acyloxy, halogen and amine, and $R^9$, $R^{10}$ and $R^{11}$ are selected from Z and $R^7$ and n is an integer equal to 1–2000 inclusive.

The silanol terminated polydiorganosiloxane-polyimide copolymers which can be made by using the above silicon-norbornane imides of formula (2) comprise by weight from 1 to 99% of polyimide blocks of the formula,

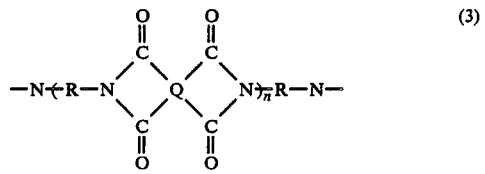 (3)

chemically combined with from 99% to 1% of polydiorganosiloxane blocks of the formula,

 (4)

where R-$R^7$, Y, Q, n and m are as previously defined.

STATEMENT OF THE INVENTION

The silicon-norbornane imides of formula (2) of the present invention can be made by initially forming a norbornene terminated polyimide by effecting reaction between organic diamine, a norbornene anhydride and organic dianhydride, in accordance with the following equation:

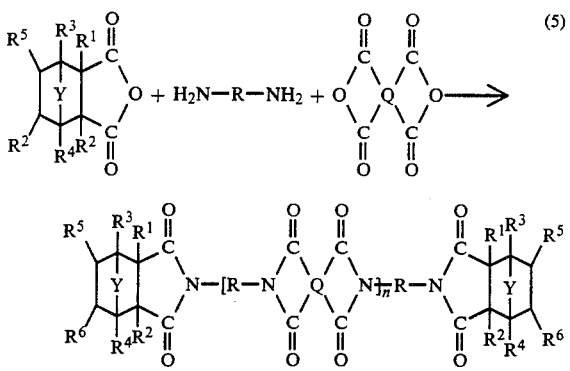

where Q, R, $R^1$-$R^6$, n and Y are as previously defined.

The aliphatically unsaturated polyimide of formula (5) or monoimide of the formula

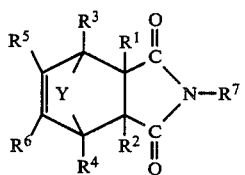

where $R^1$-$R^7$ and Y are as previously defined, can thereafter be hydrosilated with a silicon hydride having the formula,

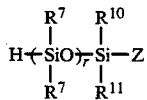

where $R^7$, $R^{10}$, $R^{11}$, r and Z are as previously defined, to produce a silicon-norbornaneimide of formula (2), or silicon-norbornane monoimide of the formula,

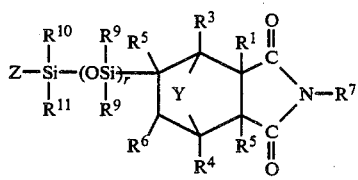

where $R^1$-$R^7$-$R^9$, $R^{10}$, $R^{11}$, r, Y and Z are as previously defined.

The silanol terminated polydiorganosiloxane polyimide copolymers which can be made in accordance with the practice of the present invention have the formula,

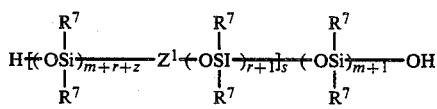

where $Z^1$ is a divalent group shown by formula (3), can be prepared by effecting reaction between the silicon-norbornanebisimide of formula (2) and a silanol terminated polydiorganosiloxane of formula (1), in the presence of an effective amount of condensation catalyst as defined hereinafter, where $R^7$, $R^9$ r and m are as previously defined and s is an integer having a value of from about 1 to $10^4$ inclusive.

Radicals included within $R^1$-$R^6$ of formulas 1, 3 and 4 are, for example, hydrogen, methyl, ethyl, propyl, butyl, etc. Radicals included within $R^7$ are, for example, aryl radicals and halogenated aryl radicals, for example, phenyl, chlorophenyl, tolyl, xylyl, biphenyl, naphthyl, etc.; alkenyl radicals, for example, vinyl, allyl, cyclohexenyl, etc.; $C_{(1-8)}$ alkyl radicals and halogenated alkyl, for example, methyl, ethyl, propyl, butyl, octyl, etc.

There are included within the silicon hydride of formula (7) triethoxysilane, dimethylchlorosilane, N,N-dimethylaminodimethylsilane, etc.

Curing agents also can be utilized in the practice of the present invention in combination with the above-described condensation vulcanizable compositions. For example, there can be used methyltriacetoxysilane, methyl-tris(2-ethylhexanoxy)silane, and a curing agent having the formula,

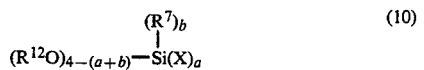

where $R^7$ is as previously defined, $R^{12}$ is a $C_{(1-8)}$ aliphatic organic radical selected from the group consisting of alkyl, alkylether, alkylester, alkylketone, and alkylcyano radicals, or $C_{(7-13)}$ aralkyl radical, X is a hydrolyzable leaving group selected from the group consisting of acyloxy, amido, amino, carbamato, enoxy, halo, imidato, isocyanato, ketoximato, oximato, thioisocyanato and ureido radicals and b is a whole number equal to 0 or 1, a is a whole number equal to 0 to 4 inclusive and the sum of a+b is equal to 0 to 4 inclusive.

In addition to curing agents of formula (10), there also can be utilized in the condensation vulcanizable compositions of the present invention alkoxy functional cross-linking agents of the formula

where $R^7$, $R^{12}$ and b are as previously defined.

Condensation catalysts can be used in the practice of the present invention to facilitate the cure of the condensation vulcanizable compositions and in certain cases facilitate the condensation of the silanol terminated polydiorganosiloxane of formula (1) with the silicon-norbornane imide of formula (2). For example, there can be used from 0.001 to 1 part of condensation catalyst, based on 100 parts of the above described silanol terminated polydiorganosiloxane-polyimide copolymer. There are included as condensation catalysts tin compounds, for example, dibutyltindilaurate; dibutyltindiacetate; dibutyltindimethoxide; carbomethoxyphenyl tin tris-uberate; tin octoate; isobutyl tin triceroate; dimethyl tin dibutyrate; dimethyl tin dineodeconate; triethyl tin tartrate; dibutyl tin dibenzoate; tin oleate; tin naphthenate; butyltintri-2-ethylhexoate; tinbutyrate. The preferred condensation catalysts are tin compounds and dibutyltindiacetate is particularly preferred.

Titanium compounds also can be used and are, for example, 1,3-propanedioxytitanium bis(ethylacetoacetate); 1,3-propanedioxytitanium bis(acetylacetonate);

diisopropoxytitanium bis(acetylacetonate); titanium naphthenate; tetrabutyltritanate; tetra-2-ethylhexyltitanate; tetraphenyltitanate; tetraoctadecyltitanate; ethyltriethanolaminetitanate. In addition, beta-dicarbonyltitanium compounds as shown by Weyenberg U.S. Pat. No. 3,334,067 can be used as condensation catalysts in the present invention.

Zirconium compounds, for example, zirconium octoate, also can be used.

Further examples of metal condensation catalysts are, for example, lead 2-ethyloctoate; iron 2-ethylhexoate; cobalt 2-ethylhexoate; manganese 2-ethylhexoate; zinc 2-ethylhexoate; antimony octoate; bismuth naphthenate; zinc naphthenate; zinc stearate.

Examples of nonmetal condensation catalysts are hexylammonium acetate and benzyltrimethylammonium acetate.

In addition to the above described one-package condensation vulcanizable curing agents, there also can be used in the practice of the present invention, curing agents which can be added to the silanol terminated polydiorganosiloxane-polyimide copolymer to provide two-package condensation vulcanizable compositions as shown in Nitzsche et al, U.S. Pat. No. 3,127,363, incorporated herein by reference.

Some of the organic dianhydrides which can be used in the practice of the present invention to produce the norbornene terminated polyimide of formula (5) along with norbornene anhydride chain-terminating monomers are, for example, benzophenone dianhydride, pyromellitic dianhydride, 2,2-bis[4-(3,4-dicarboxyphenoxy)phenyl]propane dianhydride, 2,2-bis[4-(2,3-dicarboxyphenoxy)phenyl]propane dianhydride, 4-(2,3-dicarboxyphenoxy)-4'-(3,4-dicarboxyphenoxy)diphenyl-2,2-propane dianhydride, and bisnorbornanesiloxane dianhydride of the formula,

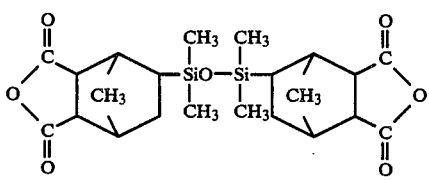

and mixtures thereof.

Organic diamines which can be used to make the polyimide blocks of the silanol terminated polydiorganosiloxane-polyimide copolymers are, for example,
o-phenylenediamine;
m-phenylenediamine;
p-phenylenediamine;
4,4'-diaminodiphenylpropane;
4,4'-diaminodiphenylmethane (commonly named 4,4'-methylenedianiline);
4,4'-diaminodiphenyl sulfide (commonly named 4,4'-thiodianiline);
4,4'-diaminodiphenyl ether (commonly named 4,4'-oxydianiline);
1,5-diaminonaphthalene;
3,3'-dimethylbenzidine;
3,3'-dimethoxybenzidien;
2,4-bis(β-amino-t-butyl)toluene;
1,3-diamino-4-isopropylbenzene;
1,2-bis(3-aminopropoxy)ethane;
benzidine;
m-xylylenediamine;
p-xylylenediamine;
2,4-diaminotoluene;
2,6-diaminotoluene;
bis(4-aminocyclohexyl)methane;
3-methylheptamethylenediamine;
4,4-dimethylheptamethylenediamine;
2,11-dodecanediamine;
2,2-dimethylpropylenediamine;
octamethylenediamine;
3-methoxyhexamethylenediamine;
2,5-dimethylhexamethylenediamine;
2,5-dimethylheptamethylenediamine;
3-methylheptamethylenediamine;
5-methylnonamethylenediamine;
1,4-cyclohexanediamine;
1,12-octadecanediamine;
bis(3-aminopropyl)sulfide;
N-methyl-bis(3-aminopropyl)amine;
hexamethylenediamine;
heptamethylenediamine;
nonamethylenediamine;
decamethylenediamine;
bis(3-aminopropyl)tetramethyldisiloxane;
bis(4-aminobutyl)tetramethyldisiloxane,
and mixtures of such diamines.

Some of the silicon hydrides of formula (7) which can be employed in the practice of the present invention to introduce silicon hydride functional groups into the polyimide having aliphatically unsaturated norbornene groups are, for example, triethoxysilane, dimethylchlorosilane, N,N-dimethylaminodimethylsilane, etc.

Silanol terminated polydiorganosiloxanes of formula (1) which can be used in combination with the silicon-norbornaneimides of formula 2 or 8 or mixtures thereof, to produce the silanol terminated polydiorganosiloxane-polyimide copolymer such as formula (9) preferably have a viscosity in the range of from about 10 to 400,000 centipoise and preferably from about 1000 to about 250,000 centipoise when measured at about 25° C. These silanol terminated fluids can be made by treating a higher molecular weight organopolysiloxane, for example, a dimethylpolysiloxane with water in the presence of a mineral acid or base catalyst. Hydrolysis of diorganohalosilane, for example, dimethyldichlorosilane, diphenyldichlorosilane, methylvinyldichlorosilane, methylfluoropropyldichlorosilane, methylcyanoethyldichlorosilane, or mixtures thereof can produce low molecular weight polymer. Equilibration thereafter can provide for higher molecular weight organopolysiloxane. Organopolysiloxane also can be treated with steam under pressure or other procedures described in U.S. Pat. No. 2,607,792 and U.K. Pat. No. 835,790.

Some of the condensation catalysts which can be used to make the silanol terminated polydiorganosiloxane polyimide copolymer of formula (9) are platinum catalysts, for example, platinum complexes of unsaturated siloxanes, as shown by Karstedt U.S. Pat. No. 3,775,442, Ashby U.S. Pat. Nos. 3,159,601, and 3,159,662 and Lamoreaux U.S. Pat. No. 3,220,972, assigned to the same assignee as the present invention. An effective amount of a platinum, catalyst is about $10^{-4}\%$ to 0.1% by weight of platinum, based on the weight of curable hydrosilylation mixture.

Various fillers and pigments can be incorporated into the room temperature vulcanizable compositions of the present invention. For example, there can be used, titanium dioxide, zirconium silicate, silica aerogel, iron oxide, diatomaceous earth, fumed silica, carbon black, precipitated silica, glass fibers, polyvinyl chloride, ground quartz, calcium carbonate, etc. The amounts of filler used can obviously be varied within wide limits in accordance with the intended use. For example, in some sealant applications, the curable compositions of the present invention can be used free of filler. In other applications, such as the employment of the curable compositions for making binding material on a weight basis, as much as 700 parts or more of filler, per 100 parts of polydiorganosiloxane-polyimide copolymers can be employed. In such applications, the filler can consist of a major amount of extending materials, such as ground quartz, polyvinyl chloride, or mixtures thereof, preferably having an average particle size in the range of from about 1 to 10 microns.

The condensation vulcanizable compositions of the present invention also can be employed as construction sealants and caulking compounds. The exact amount of filler, therefore, will depend upon such factors as the application for which the organopolysiloxane composition is intended, the type of filler utilized (that is, the density of the filler and its particle size). Preferably, a proportion of from 5 to 300 parts of filler, which can include up to about 35 parts of reinforcing filler, such as fumed silica filler, per 100 parts of silanol terminated organopolysiloxane is utilized.

The silicon-norbornaneimides of formulas (2) and (8) can be used as an adhesion promoter in room temperature vulcanizable organopolysiloxane compositions.

There are included within the silicon-norbornane monoimide of formula (8), compounds such as

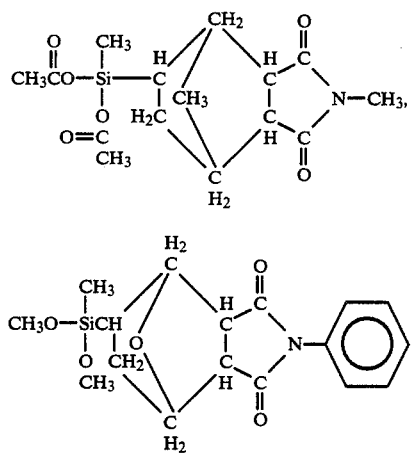

Additional compounds which are the above compounds with chlorine or amine radicals attached to silicon.

In the practice of one form of the present invention, the silicon-norbornanebisimide can be reacted with silanol terminated polydiorganosiloxane to produce the silanol terminated polydiorganosiloxane-polyimide copolymer of formula (9) referred to hereinafter as the "silanol polyimide copolymer". The silanol polyimide copolymer can thereafter be used to make condensation vulcanizable polydiorganosiloxane-polyimide copolymer compositions by mixing the curing agent, condensation catalyst and optionally cross-linking agent with the silanol polyimide copolymer.

There can be utilized in the condensation vulcanizable compositions of the present invention, an effective amount of the curing agent as previously defined which may vary depending upon whether a one-package or two-package is desired, or whether the curing agent utilized will generate an acidic or substantially neutral by-product. For example, in instances where an acyloxy curing agent is used, such as methyltriacetoxysilane, effective results can be achieved if from 0.002 to 10 parts of methyltriacetoxysilane per 100 parts of the silanol-polyimide copolymer is used. A curing agent, such as shown by formula (10), can be utilized at from 0.002 to 10 parts of curing agent per 100 parts of the silanol-polyimide copolymer. A cross-linking agent, as shown by formula (11) also can be used in combination with the curing agent of formula (10) in proportions of from 0 to 10 parts of cross-linking agent per 100 parts of the silanol-polyimide copolymer. Condensation catalyst also can be used in the proportions as previously defined.

As taught previously, the above-described condensation vulcanizable compositions also can be combined with various fillers, pigments and extenders which can be optionally incorporated into the silicone-polyimide copolymer prior to, along with, or after the incorporation of the curing agent, condensation catalyst, etc.

The synthesis of the norbornene terminated polyimide of formula (5) or the corresponding monoimide can be accomplished by conventional procedures, utilizing substantially equal molar amounts of the organic diamine dianhydride along with an effective amount of the chain-stopping norbornene anhydride or the latter with organic amine such as methyl amine or other $C_{(1-8)}$ alkyl amine aniline, etc., which can be utilized in an amount sufficient to produce the polyimide at a desired molecular weight. During the polymerization of the norbornene terminated polyimide, there can be utilized organic solvents, for example, orthodichlorobenzene, and temperature in the range of from 140° C. to 200° C. can be employed. Reaction can be conducted in an inert atmosphere, for example, under nitrogen to minimize undesirable side reactions. Reaction times can vary from 30 minutes or less to 3 hours, depending upon the nature of the reactants, the molecular weight of the polyimide desired, etc.

The silicon-norbornanebisimide of formula (2) or monoimide of formula (8) can be synthesized by effecting reaction between the appropriate norbornene imide and an appropriate silicon hydride of formula (7), in the presence of an effective amount of a platinum catalyst. An effective amount of platinum catalyst is from about $10^{-6}$ parts to $10^{-3}$ parts of platinum, per part of the hydrosilylation mixture consisting of the norbornene terminated polyimide, silicon hydride and an inert organic solvent which can be utilized in an amount sufficient to produce a mixture having from 10% to 50% by weight of solids. Suitable inert organic solvents which can be used are, for example, chlorobenzene and orthodichlorobenzene. Hydrosilylation is preferably conducted under substantially anhydrous conditions at a temperature in the range of from 15° C. to 90° C.

The preparation of the silanol-polyimide can be achieved by effecting reaction between the silicon-norbornaneimide of formula (2) and the silanol-terminated polydiorganosiloxane of formula (1) at a temperature in the range of from 15° C. to 150° C. in the presence of an effective amount of copolymerization catalyst. Suitable copolymerization catalysts include for example, amine, alkali metal fluoride, colloidal nickel, zinc chloride, platinum, or rhodium complexes, dibutyltindiacetate, with or without an aprotic solvent to facilitate reaction, such as dichloromethane, chlorobenzene, orthodichlorobenzene, etc, depending upon the mutual solubility of the reactants.

The condensation vulcanizable silicon-polyimide compositions also can be blended with silanol-terminated polydiorganosiloxane of formula (2) as described above. The blending can be accomplished under substantially anhydrous conditions at a temperature in the range of from about 15° C. to about 200° C. or higher. The resulting cured silicon-polyimide copolymers can be utilized in a variety of applications requiring high strength, high performance, temperature resistant elastomers.

In order that those skilled in the art will be better able to practice the invention, the following examples are given by way of illustration and not by way of limitation. All parts are by weight.

EXAMPLE 1

A solution of 6.56 grams of norbornene dicarboxyldianhydride, 20.8 grams of 2,2-bis[4-(3,4-dicarboxyphenoxy)phenyl]propane dianhydride and 6.48 grams of meta-phenylenediamine was refluxed in 100 ml of dry chlorobenzene for three hours. During the reflux period, water was continuously removed azeotropically. After some of the solvent was removed under reduced pressure, the residue was poured into 600 ml of methanol and stirred vigorously. A precipitate was collected which was washed with methanol and dried. There was obtained 31 grams of product. A 98% yield of an oligomer was recovered having the formula

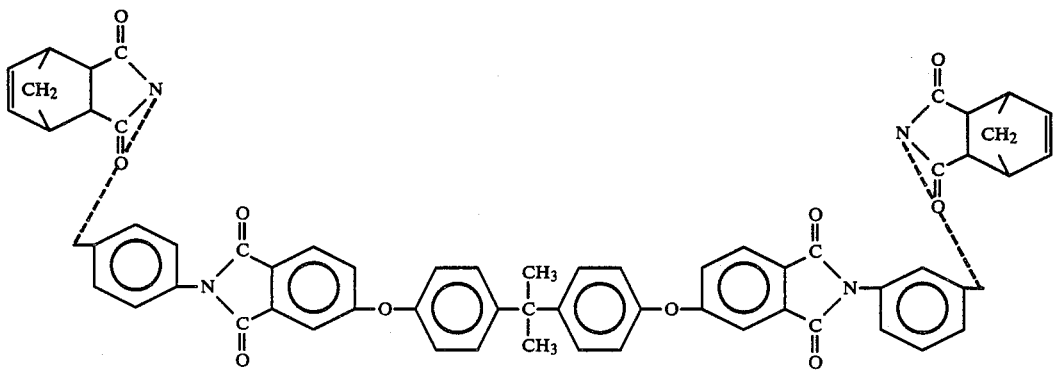

There was added 5 drops of a 5% platinum catalyst prepared in accordance with Karstedt, U.S. Pat. No. 3,775,442 to a solution of 2 grams of the above norbornene terminated oligoimide, 0.3 grams of dimethylchlorosilane in 30 ml of dry chlorobenzene. The addition was performed under substantially dry conditions. The solution was heated to 80° C. over a period of about 12 hours under sealed conditions. Based on method of preparation there was obtained a dimethylchlorosilylnorbornane end-stopped oligomide corresponding to the norbornene terminated oligomide shown above which was confirmed by NMR. After excess dimethylchlorosilane was removed from the mixture, there was added 0.4 grams of sodium acetate and the mixture was stirred at ambient conditions for an additional 12 hours. Carbon black was then added to the mixture which was filtered resulting in a colorless solution. Based on method of preparation and NMR spectra, there was obtained a dimethylacetoxysilylnorbornane imide end-capped oligomide having the formula,

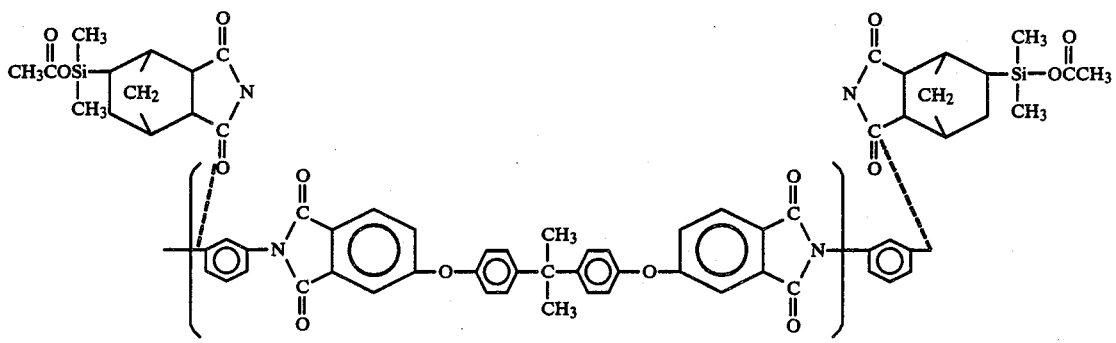

There was added to the above solution 14.5 grams of a silanol terminated dimethylpolysiloxane having 3.15 weight percent chemically combined hydroxy radicals. The resulting solution was stirred at ambient conditions for 12 hours. Upon evaporation of the volatiles of the resulting mixture, there was obtained an opaque, high viscous residue. Based on method of preparation, the product was a silanol terminated siloxane-imide block copolymer.

A blend of 2 grams of the block copolymer and 20 miligrams of methyltriacetoxysilane along with 0.1 part of dibutyltindiacetate is exposed for 1 week under 58% relative humidity. A tack-free elastomer is obtained.

EXAMPLE 2

There was refluxed for a three hour period, a solution of 9.81 grams of norbornene dicarboxylic acid monoethylester, 9.66 grams of benzophenone tetracarboxylic acid dimethylester, 9.91 grams of 4,4'-methylenedianiline and 100 ml of dry methanol. After the solvent was removed, the residue was heated to 150° C. for 3 hours under nitrogen. The resulting product was dissolved in dry chlorobenzene and then poured into methanol. There was obtained a precipitate which was collected, washed with methanol and dried in accordance with the procedure of Example 1. A yield of 98% of a product was obtained having the following formula

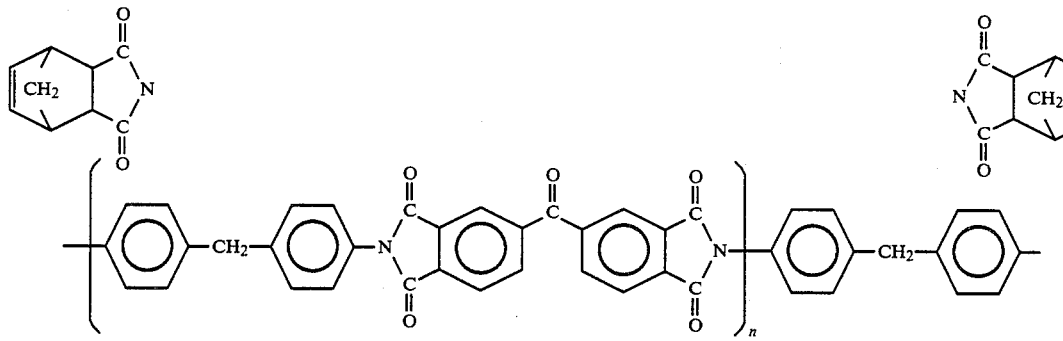

where n is 1.

A mixture of 3.14 grams of the above norborneneimide end-capped oligomide, 2 grams of triethoxysilane, 100 ml of dry chlorobenzene and 5 drops of a 5% platinum catalyst of Example 1, was heated under substantially anhydrous conditions to 80° C. over a 12 hour period. After removal of 50 ml of solvent and excess triethoxysilane, the residue was poured into 100 ml of dry ethylether. There was obtained 3.96 grams, or 96% yield of a triethoxysilyl end-capped oligomide. After the product was collected, washed with diethylether and dried. The identity of the product was confirmed by $^1$H NMR. The formula of the product was as follows

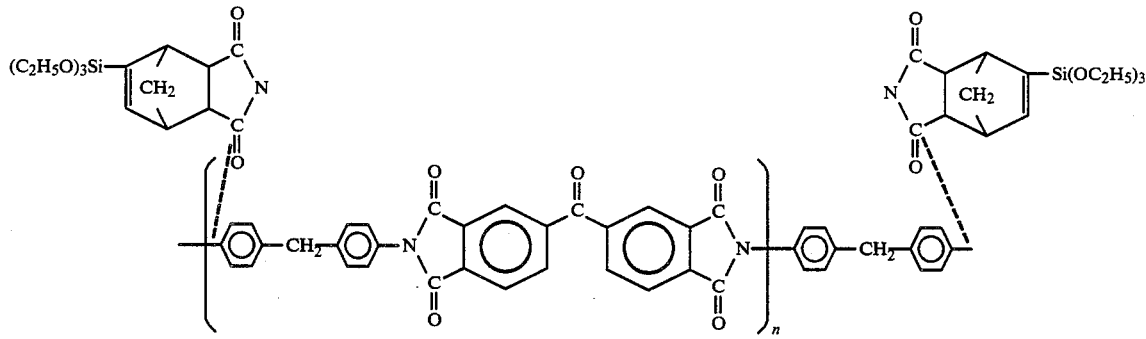

A blend of 0.3 grams of the above oligomide, 3 grams of a silanol terminated polydimethylsiloxane having a viscosity of 126,000, 200 centipoise, 0.15 grams of fumed silica and one drop of dibutyltindiacetate in 20 ml of dry methylene chloride was poured into a glass dish. After removal of the solvent, the residue was heated to 150° C. for 4 hours resulting in the formation of a cured tough elastomer exhibiting good adhesion to the glass.

EXAMPLE 3

There was mixed 4.2 grams of the norborneneimide end-capped oligomide of Example 2 with 3 grams of dimethylchlorosilane, 100 ml of chlorobenzene and 5 drops of the 5% platinum catalyst of Example 1 under nitrogen. The resulting mixture was heated to 80°–100° C. for 24 hours. After removal of unreacted dimethylchlorosilane, the residue was slowly added to a solution of dimethylamine to a solution of 2 grams of dimethylamine in 20 ml of chlorobenzene at about 0° C. The resulting mixture was stirred at room temperature for a period of 12 hours. Carbon black was then added to the solution and the mixture was further stirred for 2 more hours. Filtration of the mixture resulted in a clear filtrate of a dimethylaminosilane terminated oligomide having the formula,

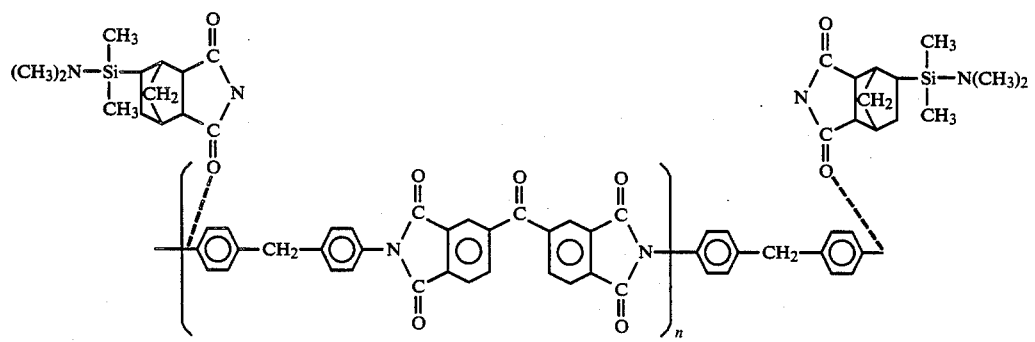

The identity of the above product was confirmed by NMR. The above filtrate was slowly added to a solution of 44 grams of a silanol terminated polydimethylsiloxane having about 3.15 weight percent of silanol at 80° C. over an addition period of about 40 minutes. The resulting opaque mixture was further stirred at 80° C. until evolution of dimethylamine had ceased. The resulting solution was then washed with water several times and volatiles were removed from the mixture under reduced pressure. There was obtained an opaque residue which was a silanol terminated siloxane imide block copolymer having an intrinsic viscosity in chloroform of about 28,500 centipoises. The block copolymer was mixed with 1½ grams of methyltriacetoxysilane in 0.3 gram of dibutyltindiacetate under substantially anhydrous conditions.

The resulting mixture was exposed at room temperature for about 1 week under a 58% relative humidity. There was obtained an opaque elastomer having a tensile strength (psi) of 139 and an elongation (percent) of 500.

Although the above examples are directed to only a few of the very many variables within the scope of the present invention it should be understood that the present invention is directed to a much broader variety of silicon-norbornane imides as shown by formula (2) which can be used to make silanol terminated silicone imide block copolymers useful in making room temperature vulcanizable compositions convertible to high strength elastomers.

What I claim as new and desire to secure by Letters Patent of the United States is:

1. Silicon functionalized norbornane carboxyimides of the formula,

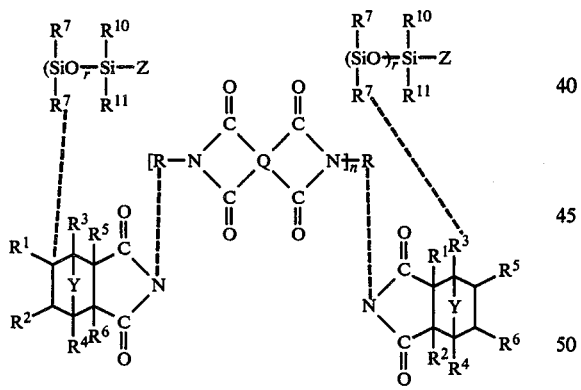

where R is a divalent radical selected from the class consisting of (a) aromatic hydrocarbon radicals having from 6–20 carbon atoms and halogenated aromatic hydrocarbon radicals having from 6–20 carbon atoms, (b) alkylene radicals having from 2–20 carbon atoms and cycloalkylene radicals having from 2–20 carbon atoms, (c) $C_{(2-8)}$ alkylene terminated polydiorganosiloxane, and (d) radicals included by the general formula,

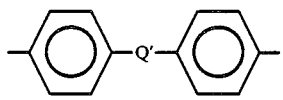

Q' is a member selected from the class consisting of

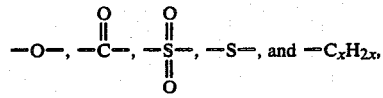

x is a whole number from 1 to 5 inclusive, Q is a tetravalent radical selected from

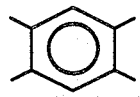

and

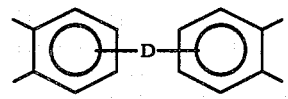

where D is a member selected from

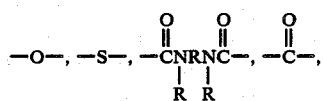

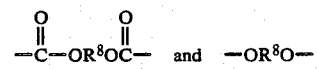

and $R^8$ is a divalent radical selected from

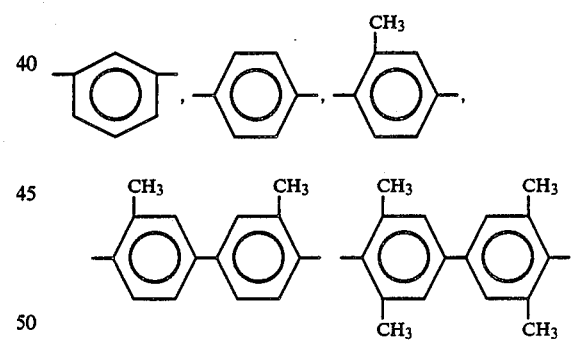

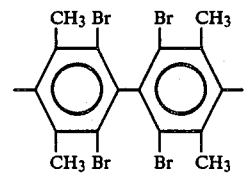

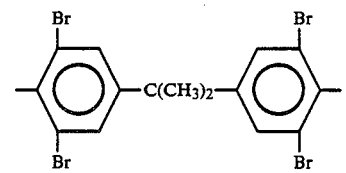

and divalent organic radicals of the general formula,

17

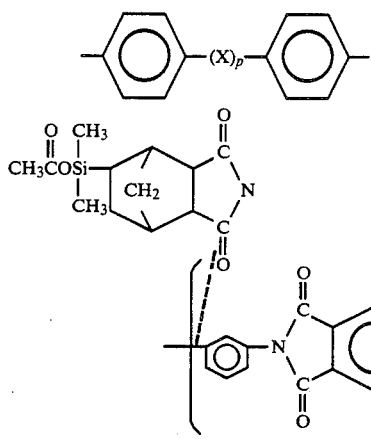

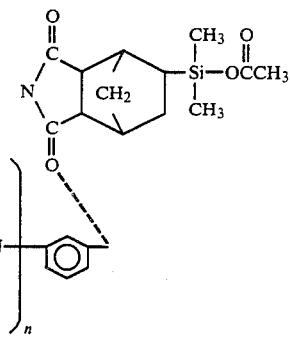

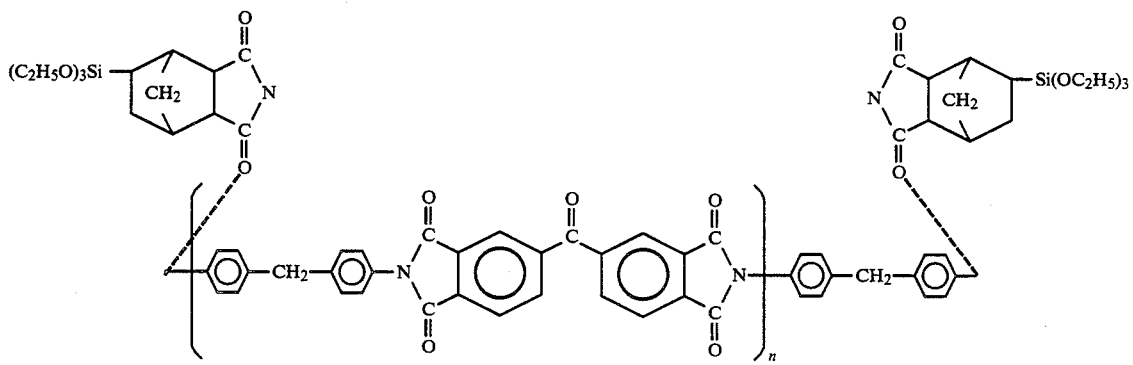

X is a member selected from the class consisting of divalent radicals of the formula,

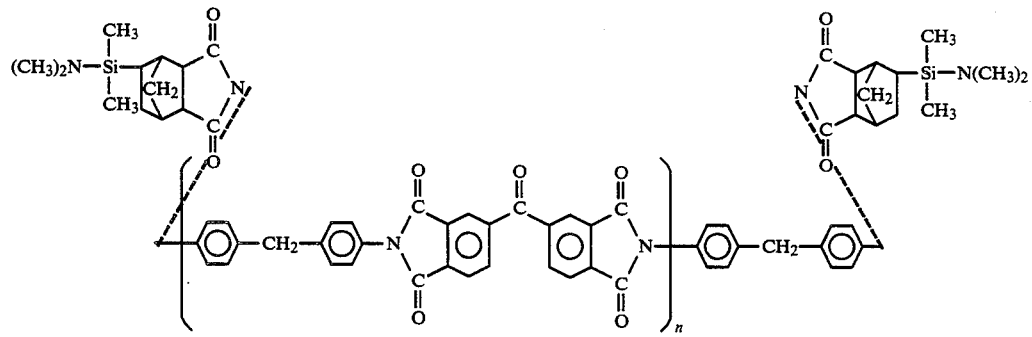

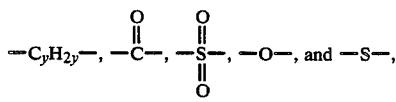

y is an integer from 1 to 5, $R^1$–$R^6$ are selected from hydrogen and $C_{(1-8)}$ alkyl radicals, $R^7$ is the same or different $C_{(1-13)}$ monovalent hydrocarbon radical and substituted $C_{(1-13)}$ monovalent hydrocarbon radical, Y is a divalent radical selected from —O— and —C($R^1$-)$_2$—, Z is selected from $C_{(1-8)}$ alkoxy, acyloxy, halogen and amine, n is an integer equal to 0–200 inclusive, and

18 p is equal to 0 or 1, and $R^{10}$–$R^{11}$ are selected from Z or $R^7$.

2. A silicon functionalized carboxyimide of claim 1 having the formula

3. A silicon functionalized carboxyimide of claim 1 having the formula where n is 1.

4. A silicon functionalized carboxyimide of claim 1 having the formula where n is 1.

5. A method for making a silicon functionalized norbornane carboxyimide which comprises (1) effecting reaction in the presence of an inert organic solvent at a temperature in the range of from 15° C. to 90° C. and under substantially anhydrous conditions between an aliphatically unsaturated polyimide of the formula,

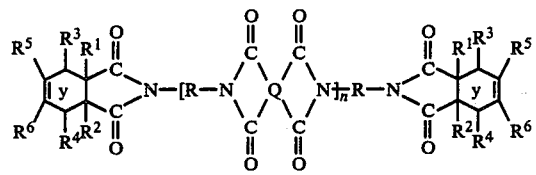

and a silicon hydride of the formula

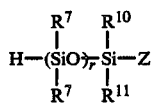

in the presence of an effective amount of a platinum catalyst, where R is a divalent radical selected from the class consisting of (a) aromatic hydrocarbon radicals having from 6–20 carbon atoms and halogenated aromatic hydrocarbon radicals having from 6–20 carbon atoms, (b) alkylene radicals having from 2–20 carbon atoms and cycloalkylene radicals having from 2–20 carbon atoms, (c) $C_{(2-8)}$ alkylene terminated polydiorganosiloxane, and (d) radicals included by the general formula,

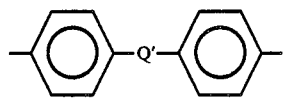

Q' is a member selected from the class consisting of

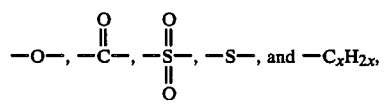

x is a whole number from 1 to 5 inclusive, Q is a tetravalent radical selected from

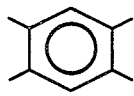

and

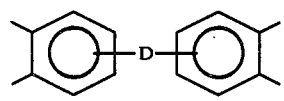

where D is a member selected from

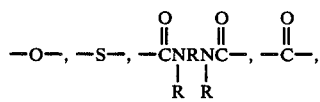

and $R^8$ is a divalent radical selected from

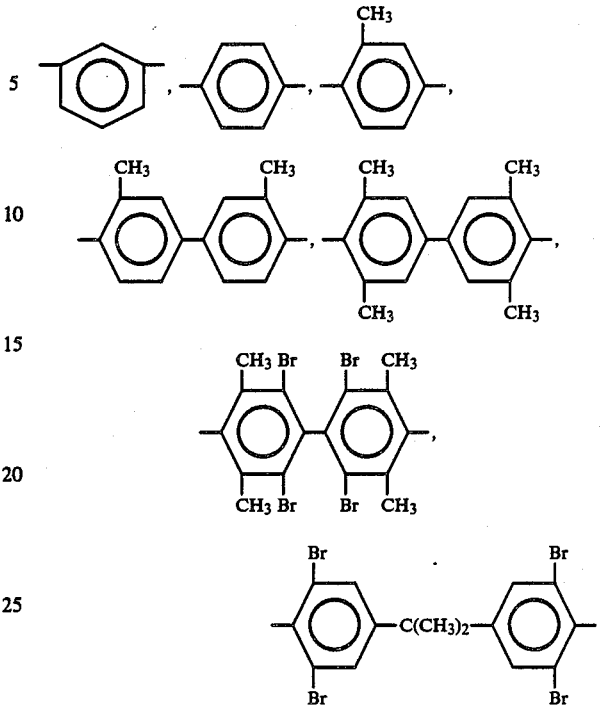

and divalent organic radicals of the general formula,

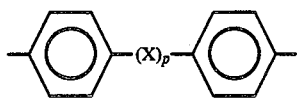

X is a member selected from the class consisting of divalent radicals of the formula,

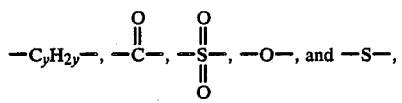

y is an integer from 1 to 5, $R^1$–$R^6$ are selected from hydrogen and $C_{(1-8)}$ alkyl radicals, $R^7$ is the same or different $C_{(1-13)}$ monovalent hydrocarbon radical and substituted $C_{(1-13)}$ monovalent hydrocarbon radical, Y is a divalent radical selected from —O— and —C($R^1$-)$_2$—, Z is selected from $C_{(1-8)}$ alkoxy, acyloxy, halogen and amine, n is an integer equal to 0–200 inclusive, and p is equal to 0 or 1, and $R^{10}$–$R^{11}$ are selected from Z or $R^7$.

6. A norbornane imide of the formula,

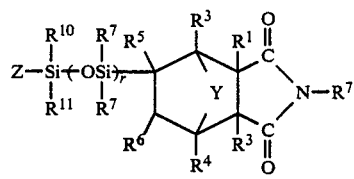

$R^1$–$R^6$ are selected from hydrogen and $C_{(1-8)}$ alkyl radicals, $R^7$ is the same or different $C_{(1-13)}$ monovalent hydrocarbon radical and substituted $C_{(1-13)}$ monovalent hydrocarbon radical and $R^{10}$–$R^{11}$ are selected from Z or $R^7$.
7. The compound
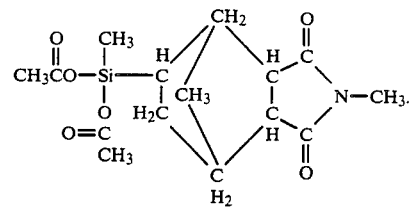
8. The compound
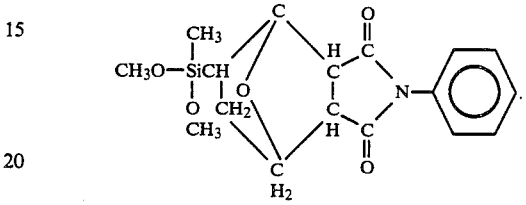
* * * * *